US006855735B2

(12) United States Patent
Friedman

(10) Patent No.: US 6,855,735 B2
(45) Date of Patent: Feb. 15, 2005

(54) KETAMINE TREATMENT OF RESTLESS LEGS SYNDROME

(75) Inventor: Robert Friedman, Haddonfield, NJ (US)

(73) Assignee: Temple University of the Commonwealth System of Higher Education, Philadelphia, PA (US)

(*) Notice: Subject to any disclaimer, the term of this patent is extended or adjusted under 35 U.S.C. 154(b) by 0 days.

(21) Appl. No.: 10/102,374

(22) Filed: Mar. 20, 2002

(65) Prior Publication Data

US 2003/0181528 A1 Sep. 25, 2003

(51) Int. Cl.$^7$ ............................ A61K 9/00; A61K 9/48; A61K 9/20; A61K 31/135; A61K 31/33

(52) U.S. Cl. ....................... 514/647; 424/400; 424/451; 424/464; 424/78.02; 514/183; 514/289; 514/450

(58) Field of Search ................................. 514/183, 289, 514/450, 654, 658, 816, 944, 964, 647, 935; 424/400, 422, 440, 451, 457, 464, 468, 78.02, 78.05

(56) References Cited

U.S. PATENT DOCUMENTS

| | | | |
|---|---|---|---|
| 5,296,507 A | 3/1994 | Tanaka et al. | |
| 5,395,831 A | 3/1995 | Gemmill, Jr. et al. | |
| 5,612,380 A | 3/1997 | Lerner et al. | |
| 5,800,385 A | 9/1998 | Demopulos et al. | |
| 5,877,173 A | 3/1999 | Olney et al. | |
| 5,976,547 A | 11/1999 | Archer et al. | |
| 6,056,715 A | 5/2000 | Demopulos et al. | |
| 6,184,218 B1 | 2/2001 | Evenden et al. | |
| 6,184,219 B1 | 2/2001 | Evenden et al. | |
| 6,194,000 B1 * | 2/2001 | Smith et al. | 424/458 |
| 6,210,394 B1 | 4/2001 | Demopulos et al. | |
| 6,248,789 B1 * | 6/2001 | Weg | 514/647 |
| 6,265,414 B1 | 7/2001 | Harris et al. | |
| 6,303,573 B1 | 10/2001 | Ruoslahti et al. | |
| 6,310,085 B1 | 10/2001 | Willis | |
| 6,316,403 B1 | 11/2001 | Pinsky et al. | |
| 6,319,927 B1 | 11/2001 | Martin | |
| 6,323,215 B1 | 11/2001 | Macielag et al. | |
| 6,350,470 B1 * | 2/2002 | Pather et al. | 424/466 |
| 6,436,974 B1 * | 8/2002 | Belliotti et al. | 514/364 |
| 2002/0072538 A1 * | 6/2002 | Chenard et al. | 514/456 |

FOREIGN PATENT DOCUMENTS

DE 4340767 * 6/1995

OTHER PUBLICATIONS

Polydefkins et al, Subclinical sensory neuropathy in late–onset restless legs syndrome, Neurology, Oct. 24, 2000 55(8): 1115–21.*

Patel (Anesthesia Anal., 70 (6), pp. 635–44, Jun. 1990).*

Bowdle et al, Psychedelic effects of ketamine in healthy volunteers: relationship to steady–state plasma concentrations, Anesthesiology. 1998, vol. 88 (1), 82–88.*

Kawasaki, Kawasaki, Ogata, Nandate and Shigematsu, "Canadian Journal of Anaesthesia," vol. 48(8), pp. 819–823 dated Sep. 2001 (Abstract Only).

Kawamata, Omote, Sonoda, Kawamata and Namiki, "Anesthesiology," vol. 93(2), pp. 520–528 dated Aug. 2000 (Abstract Only).

Radu, Bordin, Weber and Lindefors, "Brain Research," vol. 908(2), pp. 197–203 dated Jul. 27, 2001 (Abstract Only).

Tang, Rao, Hu and Wang, "Chung–Kuo Yao Li Hsueh Pao–Acta Pharmacologica Sinica," vol. 21(9), pp. 819–823 dated Sep. 2000 (Abstract Only).

Pieta, Millar, Zacharias, Fine and Kryger, "Effect of Pergolide on Restless Legs and Leg Movements in Sleep in Uremic Patients," vol. 21(6), pp. 617–622 dated Sep. 15, 1998 (Abstract Only).

Trenkwalder, Stiasny and Oertel, "Therapy of Idiopathic and Uremic Restless Legs Syndrome," vol. 67(4), pp. 265–276 dated Sep. 1996 (Abstract Only).

Montplaisir, Denesle, Petit, "Pramipexole in the Treatment of Restless Legs Syndrome: A Follow–Up Study," vol. 7 suppl. 1, pp. 27–31 dated May 2000 (Abstract Only).

Stiasny, Wetter, Trenkwalder and Oertel, "Restless Legs Syndrome and Its Treatment by Dopamine Agonists," vol. 7(1), pp. 21–25 dated Nov. 1, 2000 (Abstract Only).

Lauema, "Nocturnal Wandering Caused by Restless Legs and Short–Acting Benzodiazepines," vol. 83(6), pp. 492–493 dated Jun. 1991 (Abstract Only).

Glasauer, "Restless Legs Syndrome," vol. 39(3), pp. 125–133 dated Mar. 2001 (Abstract Only).

Earley, Allen, Beard and Connor, "Insight into the Pathophysiology of Restless Legs Syndrome," vol. 62(5), pp. 623–628 dated Dec. 1, 2000 (Abstract Only).

Freye and Levy, "Acute Abstinence Syndrome Following Abrupt Cessation of Long–Term Use of Tramadol (Ultram): A Case Study," vol. 4(3), pp. 307–311 dated 2000 (Abstract Only).

Tan and Ondo, "Restless Legs Syndrome: Clinical Features and Treatment," vol. 319(6), pp. 397–403 dated Jun. 2000 (Abstract Only).

Walters, et al., "Long–Term Follow–Up On Restless Legs Syndrome Patients Treated with Opioides," vol. 16(6), pp. 1105–1109 dated Nov. 2001 (Abstract Only).

(List continued on next page.)

Primary Examiner—Gary Kunz
Assistant Examiner—Sharmila S. Gollamudi
(74) Attorney, Agent, or Firm—Drinker Biddle & Reath LLP

(57) ABSTRACT

The present invention is directed to a method for treating symptoms associated with Restless Legs Syndrome (RLS). The method includes administering to a warm-blooded animal in need of such treatment a dose of ketamine sufficient to alleviate symptoms associated with RLS.

6 Claims, No Drawings

OTHER PUBLICATIONS

Tergau, Wischer, Wolf and Paulus, "Treatment of Restless Legs Syndrome with the Dopamine Agonist Alpha–dihydroergocryptine," vol. 16(4), pp. 731–735 dated Jul. 2001 (Abstract Only).

Danoff, Grasso, Terry and Flynn, Pleuropulmonary Disease Due to Pergolide Use for Restless Legs Syndrome, vol. 120(1), pp. 313–316 dated Jul. 2001 (Abstract Only).

Akata, Izumi and Nakashima, "Mechanisms of Direct Inhibitory Action of Ketamine on Vascular Smooth Muscle in Mesenteric Resistance Arteries," vol. 95(2), pp. 452–462 dated Aug. 2001 (Abstract Only).

Allen and Earley, "Restless Legs Syndrome: A Review of Clinical and Pathophysiologic Features," vol. 18(2), pp. 128–147 dated Mar. 2001.

Paulson, "Restless Legs Syndrome How to Provide Symptom Relief with Drug and Nondrug Therapies," vol. 55(4), pp. 35–38,43–44,47–48 dated Apr. 2000 (Abstract Only).

Evidente, Adler, Caviness, Hentz and Gwinn–Hardy, "Amantadine is Beneficial in Restless Legs Syndrome," vol. 15(2), pp. 324–327 dated Mar. 2000 (Abstract Only).

Kraus, Shuld and Pollmacher, "Periodic Leg Movements in Sleep and Restless Legs Syndrome Probably Caused by Olanzapine," vol. 19(5), pp. 478–479 dated Oct. 1999 (Abstract Only).

Adler, "Treatment of Restless Legs Syndrome with Gabapentin," vol. 20(2), pp. 148–151 dated Apr. 1997 (Abstract Only).

Chaudhuri, et al., "Restless Legs Syndrome," vol. 71(2), pp. 13–146 dated Aug. 2001.

Rastaldo, Penna and Pagliaro, "Comparison Between the Effects of Pentobarbital or Ketamine/Nitrous Oxide Anesthesia on Metabolic and Endothelial Components of Coronary Reactive Hyperemia," vol. 69(6), pp. 729–738 dated Jun. 29, 2001 (Abstract Only).

Ogawa, Tanaka and Murray, "Inhibitory Effects of Etomidate and Ketamine on Endothelium–Dependent Relaxation in Canine Pulmonary Artery," vol. 94(4), pp. 668–677 dated Apr. 2001 (Abstract Only).

Evidente and Adler, "How to Help Patients with Restless Legs Syndrome. Discerning the Indescribable and Relaxing the Restless," vol. 105(3), pp. 59–61, 65–66, 73–74 dated Mar. 1999(Abstract Only).

Lauerma and Markkula, "Treatment of Restless Legs Syndrome with Tramadol: An Open Study," vol. 60(4), pp. 241–244 dated Apr. 1999 (Abstract Only).

Ehrenberg, Eisensehr, Corbett, Crowley and Walters, "Valproate for Sleep Consolidation in Periodic Limb Movement Disorder," vol. 20(5), pp. 574–578 dated Oct. 2000 (Abstract Only).

Wetter and Pollmacher, "Restless Legs and Periodic Leg Movements in Sleep Syndromes," vol. 244 (4 Suppl. 1), pp. S37–45 dated Apr. 1997 (Abstract Only).

* cited by examiner

KETAMINE TREATMENT OF RESTLESS LEGS SYNDROME

FIELD OF THE INVENTION

The present invention relates to Restless Legs Syndrome (RLS). More specifically, it relates to a method for treating symptoms associated with RLS.

BACKGROUND OF THE INVENTION

RLS is a common, potentially disabling condition that affects about 10% to 15% of the general population and yet is often unrecognized and misdiagnosed. It is mainly diagnosed clinically and only rarely requires polysomnography. The condition is usually primary and treatable. First, however, secondary causes should be sought, especially iron deficiency and peripheral neuropathy, because when the source is an accompanying factor or condition, the syndrome may be curable.

RLS is a life-long condition for which there is no cure. Symptoms may gradually worsen with age, and their most disabling feature is the sleep onset insomnia they cause, which can be severe. RLS is a sensori-motor (movement) disorder characterized by uncomfortable sensations in the legs, which are worse during periods of inactivity or rest or while sitting or lying down. There is often a positive family history of the disorder. Individuals affected with the disorder describe the sensations as pulling, drawing, crawling, wormy, boring, tingling, pins and needles, prickly, and sometimes painful sensations that are usually accompanied by an overwhelming urge to move the legs. Sudden muscle jerks may also occur. Movement provides temporary relief from the discomfort. In rare cases, the arms may also be affected. Symptoms may interfere with sleep onset (sleep onset insomnia). Research suggests that RLS is related to periodic limb movement disorder (PLMD), another more common motor disorder which causes interrupted sleep. The symptoms often exhibit circadian rhythmicity in their peak occurrence during awakening hours.

A variety of etiologies have been proposed for RLS including pregnancy, polyneuropathy, spinal stenosis, Parkinson's disease, peripheral microembolism, and drug withdrawal from sedatives and vasodilators. While many mechanisms have been proposed for RLS, inflammation in the central nervous system associated and impaired blood flow to spinal nerve roots seems to be a common theme. RLS might result from the accumulation of irritants in the legs that are removed by leg movements. Changes in nerve conduction tests have also been reported in patients with RLS, suggesting abnormalities in spinal cord function. It has also been reported to reflect an autosomal dominant expression in families.

RLS has occurred in patients with and without painful neuropathies, and with alcoholic neuropathy, a painless neuropathy. RLS is not uniformly improved with analgesic drugs, like opioids, anti-convulsants, and others. RLS is improved with drugs used for treatment of movement disorders and not thought to have any analgesic properties (pergolide).

RLS is an independent predictor of mortality in dialysis patients, affecting up to 30%. There is no data available on whether this disrupter of sleep contributes to excess mortality in obese, diabetic, older females group outside of dialysis patients with greatest prevalence of RLS.

Neuroinflammation, which can contribute to chronic pain, may explain some of the mechanisms suggested for RLS. Neuroinflammation involves activation of endothelial cells, microglia and astrocytes, with subsequent production of cytokines, chemokines and the expression of surface antigens that enhance the immune, inflammatory and excitotoxic cascades. Activated glial cells synthesize proinflammatory mediators that act through NMDA receptors to enhance pain. At the spinal cord level, glial activation leads to the release of cytokines, chemokines and adhesion molecules. Alterations in blood flow and glial function in the central nervous system has been identified in pre-clinical acute and chronic pain studies.

Ketamine, a noncompetive N-methyl-D-aspatate (NMDA) receptor antagonist, in clinical use for almost 35 years, but has only recently been used in pain treatment. Ketamine is metabolized by hepatic cytochrome P450 system. The primary metabolite of oral ketamine is norketamine, which though one-third to one-fifth as potent as ketamine, contributes significantly to analgesia. Ketamine interacts with NMDA and a variety of other receptors, which affect analgesia. Ketamine inhibits activation of the NMDA receptor by glutamate, an excitatory neurotransmitter in CNS. Ketamine also reduces the presynaptic release of glutamate and potentiates the effects of the inhibitory neurotransmitter, GABA.

Inflammatory mediators produced locally by compression of nerve roots can activate neutrophils that then adhere to blood vessels and impair blood flow. Ketamine suppresses neutrophil production of inflammatory mediators and improve blood flow. Ketamine reduces the migration of leukocytes through endothelial cells due to influence on adhesion molecule expression. Direct inhibition of proinflammatory cytokines in the human whole blood by ketamine may also account for its anti-inflammatory actions.

Treatment for RLS is symptomatic. Massage and application of cold compresses may provide temporary relief. The most effective drugs are dopaminergic agents, clonazepam, opioids, gabapentin and clonidine. Additional agents are available that may be beneficial as add-on or alternative therapy. Medications such as temazepam, levodopa/carbidopa, bromocriptine, pergolide mesylate, oxycodone, propoxyphene and codeine are effective in relieving the symptoms. None of the existing treatments have anti-inflammatory effects. However, many of these medications have side effects. Accordingly, a method for treating the symptoms associated with RLS is needed which does not pose an undue risk of the occurrence of side effects and uses a different mode of action.

SUMMARY OF THE INVENTION

The method for treating symptoms associated with RLS of the present invention comprises administering to a warm-blooded animal, such as a human, in need of such treatment, a dose of ketamine sufficient to alleviate symptoms associated with RLS.

In general, a human in need of such treatment is one which has or expresses symptoms associated with RLS as described above. The doses of ketamine that are administered according to the method of the present invention are suitably low levels of ketamine which are below those which produce psychotomimetic side effects or are used for pain relief or control.

It is to be understood that both the foregoing general description and the following detailed description are exemplary, but not restrictive, of the invention.

DETAILED DESCRIPTION OF THE INVENTION

The present invention is directed to a method for treating symptoms associated with RLS. The method of the present invention comprises administering to a warm-blooded animal, such as a human, in need of such treatment, a dose of ketamine sufficient to alleviate symptoms associated with RLS. A human in need of such treatment is one which has or expresses symptoms associated with RLS.

According to the present invention, the term "ketamine" refers to ketamine [(2-o-chlorophenyl)-2-(methylamino)-cyclohexanone], metabolites of ketamine, such as norketamine, pharmaceutically acceptable salts thereof, such as ketamine tannate, ketamine maleate, ketamine hydrochloride, etc., and biologically equivalent derivatives and analogs thereof, such as ketamine aspartate, ketamine succinate, etc. Other names for ketamine include ketaject, ketalar, ketanest, ketaset, ketalar, calypos, and feldeross. Also included within the scope of the term "ketamine," as one of ordinary skill would presume, are isomers and enantiomers thereof that demonstrate RLS-symptom treating properties.

According to the present invention, the partial sentence "a dose of ketamine sufficient to alleviate symptoms associated with RLS" is used to describe a dose that is generally effective in alleviating, reducing, noticeably reducing, or eliminating, symptoms associated with RLS. The dose of ketamine that is administered generally will depend on the size of the subject being treated. A typical oral dose of ketamine that is administered in the method is suitably less than about 0.1 mg/kg of body weight, although greater doses may be employed if desired or necessary, for example up to about 1 mg/kg of body weight. Each typical dose of ketamine that is administered in the method is suitably from about 2 mg to about 50 mg, although greater doses may be employed if desired or necessary. A suitable daily dose is one in the range of about 2 mg to about 100 mg.

Doses of ketamine far lower than those used in the treatment of other disorders are beneficial for subjects suffering from RLS, in order to minimize the psychotomimetic side effects commonly associated with the use of the higher doses of ketamine. Also, it is suitable that the dose of ketamine administered is less than the dose generally administered for alleviation of pain. For example, since only about 20% of an oral dose of ketamine is absorbed, the successful treatment of a patient with 2 mg of ketamine for RLS over a 24 hour period would equal less than 0.001 mg/kg/hour. At these doses, the threshold serum level for pyschotomimetic side effects (on the order of 50 ng/ml) is not reached. Moreover, the threshold serum level for pain relief (on the order of 200 ng/ml) is also not approached. Patients who have been treated with low doses of oral ketamine for RLS were found, using commercially available tests, not to have detectable serum levels of ketamine. Thus, the serum levels at which oral ketamine acts to relieve RLS are substantially lower than those reported for pain relief. Treatment with low dosages of oral ketamine provides relief for subjects suffering from or affected by RLS by alleviating symptoms associated with RLS, and avoids the side effects generally encountered in the use of ketamine for the treatment of conscious patients and/or other therapies for RLS described above.

For purposes of treatment in accordance with the present invention, it is suitable that the dose of ketamine is administered orally in a form such as a powder, a tablet, a capsule, a pill, a lozenge, a sustained release form, a liquid, a suspension, or a gel. Some examples of a sustained release form are a zero-order release form and a heat stabilized dosage form with microencapsulated ketamine. Other forms of the dose of ketamine that is administered may also be employed if desired. It is obvious to one of ordinary skill in the art that the dose of ketamine may potentially be administered intravenously, intramuscularly, transmucosally, transdermally, and by any other known means in the art, in which case the doses employed are suitably modified to take into account the ketamine bioavailability in each form of administation so that the serum level of ketamine is less than, or on the order of 50 ng/ml (taking into account that ketamine bioavailability in oral administration is on the order of 200.

The following case reports or Examples demonstrate the application of the present invention, which are provided merely by way of exemplification and are not intended to limit the invention. The first two examples report two patients with RLS who failed multiple treatments and whose symptoms were significantly improved with orally administered ketamine.

EXAMPLE 1

A 70-year old female patient presented with a history of back pain, neurogenic claudication, and RLS. Treatment with the dopaminergic agonist, pergolide and oxycodone had been ineffective. In addition to RLS, the patient's past history included prior spinal surgery, insulin-dependent diabetes mellitus, sleep apnea, and congestive heart failure. Her family history was positive for RLS.

The patient was prescribed amitriptyline 25 mg at bedtime and gabapentin 300 mg three times daily in addition to her other medications. A month later, she returned with no improvement in her symptoms and reported a verbal analog pain score (VAS) of 6/10.

After consenting to the evaluation of single dose efficacy of oral ketamine, the patient received 30 mg of ketamine mixed in 50 cc (or ml) of water. After 20 minutes of observation, the patient noted that her VAS score had improved to 2/10. The patient felt relaxed and noted no dizziness, or other distressing symptoms. The patient then continued to take oral ketamine 30 mg twice a day for 6 months thereafter, and noted improvement in sleep and RLS.

EXAMPLE 2

A 61-year old male patient with a history of chronic lower back pain, spinal stenosis, scoliosis, and RLS complained of worsening neurogenic claudication. His VAS was 7/10. He had been treated with tramadol, rofecoxib, gabapentin and quinine without success. Lumbar epidural steroid injections had also failed to relieve his RLS symptoms.

The patient was then treated with 50 mg of oral ketamine. Within 15 minutes, his VAS improved from 7/10 to 2/10 and he noted subjective improvement in walking. A month following the ketamine trial, the patient continued to take oral ketamine 40 mg twice a day, and noted significant improvement in his sleep and RLS symptoms.

EXAMPLE 3

A patient presented with a history of cardiac transplant, on immune suppressive medication, could not be treated with steroids for with spinal stenosis, neurogenic claudication, and RLS.

The patient received oral doses of 20 mg of ketamine at bedtime, and did not like psychotomimetic side effects. While the patient noted no pain relief, there was noted resolution of RLS, which persisted even after ketamine was stopped.

EXAMPLE 4

A patient presented with a history of multiple back surgeries and depression. After being put on oral daily dosages of 25 mg of ketamine the patient reported lessened RLS symptoms and improved sleep. The patient's RLS symptoms did not return even with the patient's own tapering of opioids. Opioids were restarted to control the return of the patient's back pain.

EXAMPLE 5

A patient presented with a history of a renal transplant with documented lumbar radiculopathy and severe RLS on immunosuppressive treatment. The RLS symptoms were so severe that the patient could not keep his legs still at his initial office visit. After being put on oral daily dosages of 10 mg of ketamine, the patient reported having pain relief and resolution of RLS. While the RLS remitted during 4 months of treatment with 25 mg of ketamine daily, opioids were added to the treatment for pain control.

EXAMPLE 6

A dialysis patient presented with a history of failed back surgery, spinal stenosis and severe leg pain which responded to treatment with methadone but maintained severe RLS where the patient was not able to sleep more than 2 hours/night. The patient could not tolerate 20 mg daily of oral ketamine because of psychotomimetic effects possibly related to the accumulation of 6-dihydro-norketamine that is 90% renal excreted. On a dose of 2 mg of oral ketamine at bedtime, RLS symptoms, however, were reduced more than 50% and the patient was able to sleep more than 4.5 hrs./night for the first time in 4 years with no psychotomimetic side effects.

EXAMPLES 7–23

In the Table shown below, patients were treated with doses of oral ketamine.

The patients, shown in Examples 7–23, were treated with doses of liquid oral ketamine or oral ketamine in tablet form. There were no patients who had serum levels of ketamine measured that reached the levels reported for therapeutic analgesic effect of ketamine, i.e., 200 ng/ml. In these patients with RLS, the low ketamine dosage improved related limb sensations, motor restlessness and insomnia.

Without being bound by any theory as to the operative mechanism or mode of action of ketamine in RLS, the results of the Examples described above raise the possibility that ketamine inhibits neuroinflammation in the spinal cord or at higher centers. Within the spinal cord, RLS might result from NMDA receptor activation and production of inflammatory mediators that impair blood flow in the spinal cord. It may then be hypothesized that the low doses of ketamine used in the present invention act on or block the inflammatory mediators (cytokines) that may promote neutrophil and platelet aggregation and impair blood flow.

It is to be understood that the present invention is not limited to the preferred or other embodiments described herein, but encompasses all embodiments within the scope of the following claims.

What is claimed is:

1. A method for treating Restless Legs Syndrome in a warm-blooded animal comprising administering to the warm-blooded animal a subanalgesic dose of ketamine insufficient to induce psychotomimetic side effects, such that motor restlessness, insomnia, and limb sensations associated with Restless Legs Syndrome are alleviated, said limb sensations being characterized by sensations of pulling, drawing, crawling, wormy, boring, tingling, pins and needles, or prickly.

2. The method according to claim 1, wherein the dose of ketamine is administered orally.

3. The method according to claim 2, wherein the dose of ketamine is less than about 0.1 mg/kg of body weight.

| Example | A | B | C | D | E | F | G | H | I | J |
|---|---|---|---|---|---|---|---|---|---|---|
| 7 | 36 | Yes | Yes | Yes | No | 80% | 6 | Yes | 50 | Rash |
| 8 | 24 | Yes | Yes | Yes | Yes | 70% | 8 | No | 100 | No |
| 9 | 60 | Yes | Yes | Yes | Yes | 50% | 6 | Yes | 50 | Yes |
| 10 | 36 | Yes | No | No | No | 60% | 1 | No | 25 | No |
| 11 | 36 | Yes | Yes | Yes | Yes | 70% | 5 | Yes | 50 | No |
| 12 | 72 | Yes | Yes | Yes | Yes | 40% | 2 | Yes | 25 | No |
| 13 | 36 | Yes | Yes | Yes | No | 80% | 3 | No | 60 | No |
| 14 | 4 | Yes | Yes | Yes | No | 50% | 2 | No | 20 | No |
| 15 | 12 | Yes | No | Yes | No | 80% | 1 | No | 10 | No |
| 16 | 36 | Yes | Yes | Yes | No | 60% | 5 | No | 25 | Yes |
| 17 | 24 | Yes | Yes | No | No | 60% | 2 | No | 20 | No |
| 18 | 36 | Yes | Yes | No | No | 80% | 5 | No | 20 | No |
| 19 | 15 | Yes | No | Yes | Yes | 90% | 2 | No | 25 | No |
| 20 | 12 | Yes | Yes | Yes | No | 60% | 2 | No | 60 | No |
| 21 | 48 | Yes | Yes | Yes | No | 60% | 5 | No | 25 | No |
| 22 | 48 | Yes | Yes | No | No | 70% | 1 | No | 10 | No |
| 23 | 36 | Yes | Yes | No | No | 70% | 3 | Yes | 20 | No |

(Legend of Table:
A = Duration of symtoms (months);
B = Neurogenic claudication, inability to walk more than 2 blocks without pain;
C = Failed treatment with neurontin;
D = Failed treatment with narcotic medication(s);
E = Failed nerve block;
F = VAS or visual analog scale for pain/walking ability (improvement);
G = Duration of ketamine treatment (months);
H = Pain resulting from surgery;
I = Dose of oral ketamine (mg/24 hours);
J = complications (Yes means changes in cognitive status with liquid but not with pill form))

4. The method according to claim 1, wherein the dose of ketamine produces a serum level of ketamine in the warm-blooded animal of no more than about 50 ng/ml.

5. The method according to claim 1, wherein the warm blooded animal is a human.

6. The method according to claim 2, wherein the oral dose of ketamine is administered in a form selected from the group consisting of a powder, a tablet, a capsule, a pill, a lozenge, a sustained release form, a liquid, a suspension, and a gel.

* * * * *